United States Patent [19]
Potter et al.

[11] Patent Number: 6,015,787
[45] Date of Patent: Jan. 18, 2000

[54] CELL-PERMEABLE PROTEIN INHIBITORS OF CALPAIN

[75] Inventors: David A. Potter, Brighton; Paul R. Skolnik, Sharon, both of Mass.

[73] Assignee: New England Medical Center Hospitals, Inc., Boston, Mass.

[21] Appl. No.: 08/964,302

[22] Filed: Nov. 4, 1997

[51] Int. Cl.[7] .......................... A61K 38/02; A61K 38/55; C07K 2/00; C07K 14/81
[52] U.S. Cl. .............................. 514/12; 514/13; 530/324; 530/326
[58] Field of Search ................................... 514/2, 12, 13, 514/21; 530/300, 324, 325, 326, 350

[56] References Cited

FOREIGN PATENT DOCUMENTS 395309    10/1990    European Pat. Off. .
95/34295  12/1995    WIPO .

OTHER PUBLICATIONS

Anagli et al., "Investigation of the role of calpain as a stimulus–response mediator in human platelets using new synthetic inhibitors", Biochem. J. 274:497–502, 1991.

Croall et al., "Domain Structure of Calpain: Mapping the Binding Site for Calpastatin", Biochemistry 33:13223–13230, 1994.

Emori et al., "All Four Repeating Domains of the Endogenous Inhibitor for Calcium–dependent Protease . . . ", The Journal of Biological Chemistry 263:2364–2370, 1988.

Emori et al., "Endogenous inhibitor for calcium–dependent cysteine protease contains four internal . . . " Proc. Natl. Acad. Sci USA 84:3590–3594, 1987.

Eto et al., "The Role of the Calpain–Calpastatin System in Thyrotropin–releasing Hormone–induced . . . ", The Journal of Biological Chemistry 270:25115–25120, 1995.

Fujise et al., "Specificity of the High Affinity Interaction of Protein Kinase C with a . . . ", The Journal of Biological Chemistry 269:31642–31648, 1994.

Hong et al., "Protein kinase C isoforms in muscle cells and their regulation by phorbol ester and calpain", Biochimica et Biophysica Acta 1267:45–54, 1995.

Huang et al., "Ester and Amide Derivatives of E64c as Inhibitors of Platelet Calpains", J. Med. Chem. 35:2048–2054, 1992.

Ishima et al., "Structure of the active 27–residue fragment of human calpastatin", FEBS 294:64–66, 1991.

Kawasaki et al., "Calpastatin Has Two Distinct Sites for Interaction with Calpain—Effect of . . . ", Archives of Biochemistry and Biophysics 305:467–472, 1993.

Kawasaki et al., "Identification and Characterization of Inhibitory Sequences in Four Repeating . . . ", J. Biochem. 106:274–281, 1989.

Lin et al., "Inhibition of Nuclear Translocation of Transcription Factor NF–kB by a Synthetic . . . ", Journal of Biological Chemistry 270:14255–14258, 1995.

Lin et al., "Role of Nuclear Localization Sequence in Fibroblast Growth Factor–1 . . . ", Journal of Biological Chemistry 271:5305–5308, 1996.

Liu et al., "Identification of a functionally import sequence in the cytoplasmic tail of integrin . . . ", Proc. Natl. Adac. Sci. USA 93:11819–11824, 1996.

Ma et al., "Requirement of Different Subdomains of Calpastatin for Calpain Inhibition and for Binding . . . ", J. Biochem. 113:591–599, 1993.

Ma et al., "Amino–terminal Conserved Region in Proteinase inhibitor Domain of Calpastatin Potentiates . . . ", Journal of Biological Chemistry 269:24430–24436, 1994.

Maki et al., "Inhibition of Calpain by a Synthetic Oligopeptide Corresponding . . . ", Journal of Biological Chemistry 264:18866–18869, 1989.

(List continued on next page.)

*Primary Examiner*—Jeffrey E. Russel
*Attorney, Agent, or Firm*—Fish & Richardson, P.C.

[57] ABSTRACT

The invention features fusion proteins that contain a calpastatin peptide and a signal sequence capable of delivering the fusion protein into a cell, and uses thereof.

25 Claims, 11 Drawing Sheets

OTHER PUBLICATIONS

Maki et al., "All four internally repetitive domains of pig calpastatin possess . . . ", FEBS 223:174–180, 1987.

Maki et al., "Repetitive Region of Calpastatin is a Functional Unit of the . . . ", Biochem. and Biophys. Res. Com. 143:300–308, 1987.

Maki et al., "Analysis of Structure–Function Relationship of Pig Calpastatin . . . ", Journal of Biological Chemistry 263:10254–10261, 1988.

McGowan et al., "Inhibition of Calpain in intact platelets by the thiol protease inhibitior . . . ", Biochem. and Biophys. Res. Com. 158:432–435, 1989.

Mellgren et al., "The binding of large calpastatin to biologic membranes is mediated in part by . . . ", Biochimica et Biophysica Acta 999:71–77, 1989.

Melloni et al., "Modulation of the Calpain Autoproteolysis by Calpastatin and . . . ", Biochem. and Biophys. Res. Com. 229:193–197, 1996.

Mohan et al., Purification and Properties of High Molecular Weight Calpastatin . . . , Journal of Neurochemistry 64:859–866, 1995.

Prochiantz, A., "Getting hydrophilic compounds into cells: lessons from homeopeptides", Curr. Opinion in Neurobiol. 6:629–634, 1996.

Resing et al., "Independent Reguation of Two Cytoplasmic Processing Stages of the Intermediate . . . ", Journal of Biological Chemistry 268:25139–25145, 1993.

Rojas et al., "Controlling Epidermal Growth Factor (EGF-)–stimulated Ras . . . ", Journal of Biological Chemistry 271:27456–27461, 1996.

Routtenberg, A., "Measuring Memory in a Mouse Model of Alzheimer's Disease", Science 277:839–840, 1997.

Ryan et al., "Knockout–Transgenic Mouse Model of Sickle Cell Disease", Science 278:873–878, 1997.

Saido et al., "Purification and Characterization of Protein Kinase C from Rabbit Brain", Biochemistry 31:482–490, 1992.

Shea et al., "Enhancement of Neurite Outgrowth Following Calpain Inhibition . . . ", Journal of Neurochemistry 65:517–523, 1995.

Takano et al., "Evidence for the repetitive domain structure of pig calpastatin . . . ", FEBS 208:199–202, 1986.

Uemori et al., "Characterization of a Functional Domain of Human Calpastatin", Biochem. and Biophys. Res. Com. 166:1485–1493, 1990.

Wang et al., "Development and Therapeutic Potential of Calpain Inhibitors", Adv. Exp. Med. and Biol. 389:118–152, 1990.

Yamazaki et al., "Specific Increase in Amyloid Beta–Protein 42 . . . ", Biochemistry 36:8377–8383, 1997.

Yang et al., "Analysis of Calcium–Independent Interaction between Amino–terminal . . . ", Journal of Biological Chemistry 269:18977–18984, 1994.

Yano et al., "The Effects of Calpeptin (A Calpain Specific Inhibitor) on an agonist . . . ", Thrombosis Research 71:385–395, 1993.

CELL-PERMEABLE PROTEIN INHIBITORS OF CALPAIN

This invention was funded in part by National Cancer Institutes Grant No. K08-1562-05. The government has certain rights in the invention.

BACKGROUND OF THE INVENTION

Calpains, a group of ubiquitous $Ca^{2+}$-activated cytosolic proteases, are hypothesized to participate in cytoskeletal remodeling events, cellular adhesion, shape change, and motility by the site-specific regulatory proteolysis of membrane- and actin-associated cytoskeletal proteins (Beckerle et al., *Cell* 51:569–577, 1987; Yao et al., *Am. J. Physiol.* 265(pt. 1):C36–46, 1993; and Shuster et al., *J. Cell Biol.* 128:837–848, 1995). Calpains have also been implicated in the pathophysiology of cerebral and myocardial ischemia, platelet activation, NF-kB activation, Alzheimer's disease, muscular dystrophy, cataract progression and rheumatoid arthritis.

Calpastatin is a physiological inhibitor of μ-calpain and m-calpain, which are named for their micromolar or millimolar $Ca^{2+}$ ion concentrations required in vitro for half-maximal activity. Calpastatin has four internally repeated domains, each of which independently binds a calpain molecule in its active, $Ca^{2+}$-bound conformation with high affinity (Mellgren et al., *The Regulation of Calpains by Interaction with Calpastatins*, and Maki et al., *Structure-Function Relationship of Calpastatins*, both in *Intracellular Calcium-Dependent Proteolysis*, Mellgren and Murachi, Eds, CRC Press, Boca Raton, Fla., 1990; and Yang et al., *J. Biol. Chem.* 269:18977–18984, 1994). There is considerable interest in inhibitors of calpain (Wang et al., *Trends in Pharm. Sci.* 15:412–419, 1994; Mehdi, *Trends in Biochem. Sci.* 16:150–153, 1991).

SUMMARY OF THE INVENTION

The invention features a method of inhibiting a calpain in a cell (e.g., μ-calpain and/or m-calpain). The method includes contacting the cell with an effective amount of a fusion protein having a first portion and a second portion, the first portion including a signal sequence capable of delivering the fusion protein into the cell (i.e. a eukaryotic cell), and the second portion including a calpastatin peptide or variant thereof. The calpastatin peptides and variants thereof inhibit calpain activity in a standard assay for calpain activity such as those described herein. Preferred calpastatin peptides are those described in Table 1 and biologically active variants thereof. Preferred variants are those which retain residues which are conserved among the peptides listed in Table 1.

Preferably, the calpastatin peptide includes the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18); wherein Xaa at position 1 is Glu, Asp, or Lys;
Xaa at position 2 is Lys, Glu, Ala, or Asn;
Xaa at position 5 is Glu, Lys, or Ile;
Xaa at position 6 is Arg, Lys, or Asp;
Xaa at position 7 is Asp, or Glu;
Xaa at position 8 is Asp, Val, Ser, Gly, or Glu;
Xaa at position 13 is Glu, Lys, or Asp;
Xaa at position 15 is Arg, Lys, or Gln;
Xaa at position 16 is Glu, His, Lys, or Leu; and
Xaa at position 19 is Glu, Asp, Asn, Ala, or Val.

In various preferred embodiments, the amino-terminal end of the second portion is covalently bonded to the carboxy-terminal end of the first portion by a peptide bond; the second portion has the sequence of SEQ ID NO:4; the first portion has the sequence of SEQ ID NO:3; the fusion protein has the sequence of SEQ ID NO:1; the cell is a platelet; the cell is a sickle erythrocyte; and the cell is an HIV-infected cell.

In other embodiments, the invention features a method of preventing platelet aggregation, which method includes contacting a plurality of platelets with an effective amount of a fusion protein, the fusion protein including a first portion and a second portion, the first portion including a signal sequence capable of delivering the fusion protein into the cell, and the second portion including a calpastatin peptide or variant thereof; a method of preventing platelet degranulation, which method includes contacting a plurality of platelets with an effective amount of a fusion protein, the fusion protein including a first portion and a second portion, the first portion including a signal sequence capable of delivering the fusion protein into the cell, and the second portion including a calpastatin peptide or variant thereof; a method of inhibiting or reversing erythrocyte sickling, which method includes contacting a sickle erythrocyte (i.e., an erythrocyte that displays a sickled morphology, or is susceptible to sickling) with an effective amount of a fusion protein the fusion protein, the fusion protein including a first portion and a second portion, the first portion including a signal sequence capable of delivering the fusion protein into the cell, and the second portion including a calpastatin peptide or variant thereof; and a method of inhibiting activation of HIV provirus, which method includes contacting an HIV-infected cell with an effective amount of a fusion protein, the fusion protein including a first portion and a second portion, the first portion including a signal sequence capable of delivering the fusion protein into the cell, and the second portion including a calpastatin peptide or variant thereof.

In various preferred embodiments of these methods, the amino-terminal end of the second portion is covalently bonded to the carboxy-terminal end of the first portion by a peptide bond; the second portion has the sequence of SEQ ID NO:4; the first portion has the sequence of SEQ ID NO:3; and the fusion protein has the sequence of SEQ ID NO:1.

The invention also features a fusion protein which includes a first portion and a second portion, the first portion including a signal sequence capable of delivering the fusion protein into a eukaryotic cell, and the second portion including a calpastatin peptide or variant thereof.

In various preferred embodiments, the calpastatin peptide includes the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18); wherein Xaa at position 1 is Glu, Asp, or Lys;
Xaa at position 2 is Lys, Glu, Ala, or Asn;
Xaa at position 5 is Glu, Lys, or Ile;
Xaa at position 6 is Arg, Lys, or Asp;
Xaa at position 7 is Asp, or Glu;
Xaa at position 8 is Asp, Val, Ser, Gly, or Glu;
Xaa at position 13 is Glu, Lys, or Asp;
Xaa at position 15 is Arg, Lys, or Gln;
Xaa at position 16 is Glu, His, Lys, or Leu; and
Xaa at position 19 is Glu, Asp, Asn, Ala, or Val.

In still other preferred embodiments, the amino-terminal end of the second portion is covalently bonded to the carboxy-terminal end of the first portion by a peptide bond; the second portion has the sequence of SEQ ID NO:4; the first portion has the sequence of SEQ ID NO:3; and the fusion protein has the sequence of SEQ ID NO:1.

Appropriate signal sequences include the 16 amino acid signal sequence of Kapsoi's fibroblast growth factor (AAVALLPAVLLALLAP; SEQ ID NO:3; Rojas et al., *J. Biol. Chem.* 271:27456–27461, 1996) or variants thereof which facilitate entry of a fused heterologous peptide into a eukaryotic cell.

The signal sequence can also be, e.g., the 16 amino acid signal sequence of antennapedia (RQIKIWFQNRRMKWKK; SEQ ID NO:6; Prochiantz, *Curr. Opinion in Neurobiol.* 6:629, 1996) or variants thereof which facilitate entry of a fused heterologous peptide into a eukaryotic cell.

Among the suitable calpastatin peptides are those corresponding to repeat 1 and repeat 4 of human, bovine, pig, rabbit, and rat calpastatins. These sequences are set forth in Table 1. Other suitable peptides can be designed by combining sequences within these repeats (e.g., the first 12 amino acids of human repeat 1 combined with the last 12 amino acids of rabbit repeat 4). A preferred calpastatin peptide, TIPPEY (Croall et al., *Biochem.* 33:13223–13230, 1994), is also shown in Table 1, along with some possible substitutions for some of the amino acid positions in TIPPEY. In general, it is preferred to retain highly conserved residues. Among the highly conserved residues are those underlined in the TIPPEY sequence shown in Table 1.

Additional amino acid residues may be present in the fusion protein without disrupting function. Such optional additional amino residues may be artifacts of the plasmid construction process, and may be left in place as a matter of convenience. The additional residues may also constitute an epitope tag that is used to facilitate identification and purification of the fusion protein.

TABLE 1

Calpastatin peptides

Repeat 1

| | | |
|---|---|---|
| human | EELGKREVTIPPKYRELLEKKEGI | (SEQ ID NO:8) |
| bovine | EELGKRESTPPPKYKELLNKEEGI | (SEQ ID NO:9) |
| pig | EELGKREVTLPPKYRELLDKKEGI | (SEQ ID NO:10) |
| rabbit | EELGKREVTIPPKYRELLEKKTGV | (SEQ ID NO:11) |
| rat | EALGIKEGTIPPEYRKLLEKNEAI | (SEQ ID NO:12) |

Repeat 4

| | | |
|---|---|---|
| human | DKLGERDDTIPPEYRHLLDDNGQD | (SEQ ID NO:13) |
| bovine | DKLGERDDTIPPKYQHLLDDNKEG | (SEQ ID NO:14) |
| pig | DKLGERDDTIPPEYRHLLDKDEEG | (SEQ ID NO:15) |
| rabbit | DKLGERDDTIPPEYRHLLDQGEQD | (SEQ ID NO:16) |
| rat | EKLGERDDTIPPEYRHLLDNDGKD | (SEQ ID NO:17) |
| TIPPEY: | EKLGERDDTIPPEYRLLEKKTGV | (SEQ ID NO:4) |
| Substitutions: | DE  KKEV   K KH  DDDEAI | |
| | A  I  S     QK  NQEGED | |
| |     G         NGKQG | |
| |                 N K | |
| | KN  D E   D  L  AT  D | |
| |                 VM | |

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, exemplary methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
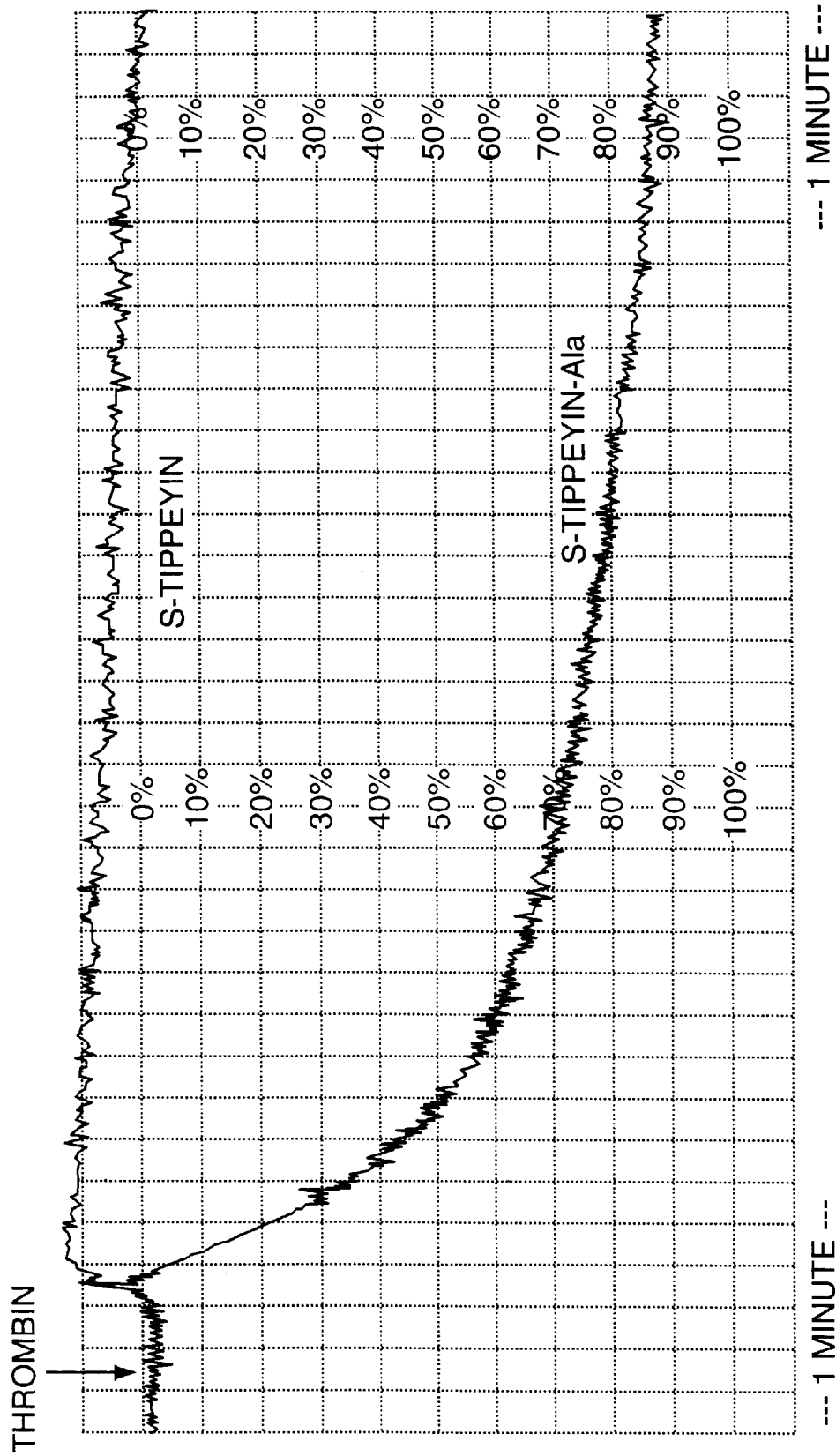
FIG. 1 is a graph showing thrombin-induced platelet aggregation in the presence of 45 $\mu$M calpastat (upper line) or S-TIPPEY-ala (lower line).

Applicants have developed soluble, cell-penetrating fusion proteins that inhibit calpain activity. These fusion proteins are composed of a cell-penetrating sequence (e.g., the signal sequence of Kapsoi's fibroblast growth factor ("kFGF")) and a biologically active derivative of calpastatin.

The sequence of one fusion protein of the invention, calpastat (also named S-TIPPEYIN), is given below. The first 16 amino acids of calpastat correspond to the kFGF signal sequence. The next 24 amino acids of calpastat correspond to a biologically active derivative of calpastatin. The fusion protein was found to lose activity when seven particular amino acid residues were substituted by alanine, as in the peptide S-TIPPEY-ala (shown below). Most of these seven amino acid residues are among those that are highly conserved in calpastatin.

```
S-TIPPEYIN (i.e., calpastat):            (SEQ ID NO:1)
NH2-AAVALLPAVLLALLAPEKLGERDDTIPPEYRELLEKKTGV-COOH S-TIPPEY-ala:                            (SEQ ID NO:2)
NH2-
AAVALLPAVLLALLAPEKLAERADAAAPEAAELLEKKTGV-COOH
```

Other fusion proteins of the invention contain a biologically active peptide fragment, or a variant thereof, of calpastatin. These fragments or variants preferably contain the consensus amino acid residues found in repeat 1 and repeat 4 of mammalian (e.g., human, bovine, pig, rabbit, and rat) calpastatins. Functional variants of the hybrid proteins that do not contain all of the consensus amino acid residues are also within the scope of the invention.

The ability of the hybrid proteins of the invention to inhibit calpain activity can be assessed in cell extracts or in intact cells as described in the examples below. Additional methods for such assessment include that disclosed by Bronk et al., *Am. J. Physiol.* 264:G744–751, 1993, and modified versions of that method. For instance, calpain activity in intact cells can be monitored by measuring $Ca^{2+}$ ionophore-specific peptidyl hydrolysis of the peptidyl-7-amino bond of the calpain substrate succinyl-leucyl-leucyl-valyn-tyrosyl-7-amino-4-methylcoumarin (suc-LLVY-AMC; SEQ ID NO:7). To do this, cells are washed and re-suspended in HEPES-buffered (10 mM HEPES-NaOH, pH 7.4) Hank's balanced salts solution (without $Ca^{2+}$) at about $2.5 \times 10^5$ cells/ml and held on ice. To assay calpain activity, the cell suspension is pre-warmed to 37° C. for 10 minutes with stirring in an SLM ALMINCO 8000 fluorimeter. At t=−1 minute, ionomycin in DMSO (2.5 $\mu$M) final concentration) or DMSO alone (negative control) is added to the cells. At t=0 minute, suc-LLVY-AMC (SEQ ID NO:7) is added to reach a concentration of 50 $\mu$M. The initial rate of substrate cleavage, which is linear, is measured by spectroscopy at 2 to 3 minutes. The excitation wavelength is 360±2 nm and the emission detection wavelength is 460±10 nM. The ionomycin-dependent rate of substrate cleavage is subtracted from the ionomycin-independent rate of subtrate cleavage to obtain the $Ca^{2+}$-dependent rate. AMC standard solutions are used to determine moles of AMC generated from emission data. Viability of cells during the assay can be monitored by trypan blue exclusion.

The fusion proteins of the invention can be produced in commercially significant amounts by well known peptide synthesis methods. The peptides can also be produced in cultured cells (e.g., *E. coli*, yeast, insect cells, or mammalian cells) that are transfected with nucleic acid molecules encoding the fusion protein and having appropriate expression control sequences (see, e.g., U.S. Pat. No. 5,648,244). The nucleic acid molecules can be introduced into the cultured cells by standard transfection techniques. Extraction and purification of recombinant peptides/polypeptides produced by tissue culture cells can be performed with techniques well known in the art, including, for example, immunoaffinity purification.

The fusion proteins of the invention can be used in reduction of coronary thrombosis in coronary bypass surgery, reduction of thrombosis and restenosis in angioplasty, reduction of infarct progression in myocardial infarction, treatment of acute myocardial infarction, reduction of infarct progression in stroke (including treatment in the acute setting), treatment of subarachnoid hemorrhage/vasospasm, treatment of muscular dystrophy, treatment of cataracts, treatment of sickle cell crisis, treatment of HIV-1 infection, treatment of Alzheimer's Disease and brain aging, treatment of traumatic brain injury, and treatment of joint inflammation/arthritis.

The fusion proteins of the invention are administered to a patient with one or more of the above-listed illnesses, or prophylactically to a patient who has not yet shown symptoms of the illnesses. For instance, the hybrid protein can be administered to a patient who has undergone angioplasty and shows signs of restenosis. Alternatively, the protein is administered before angioplasty to prevent occurrence of restenosis.

The fusion proteins of the invention can be used alone, or in a mixture, in the presence of a pharmaceutically acceptable carrier (e.g., physiological saline), which is selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences* (E. W. Martin), a standard reference text in this field, and in the USP/NF.

Alternatively, the therapeutic compositions can be formulated to include ingredients that augment or potentiate the therapeutic activity of the hybrid proteins, e.g., those that increase the biological stability of the proteins, or increase the therapeutic compositions' ability to penetrate the target cells selectively. By way of example, to enhance targeting, the peptides can be encapsulated in liposomes coated with ligands of cell-surface receptors which are primarily or exclusively present on the target cells. The selection of other ingredients will depend on considerations such as the particular disease(s) or disorder(s) for which the composition is to be used, and potential adverse drug interactions.

The therapeutic compositions of the invention can be administered in dosages determined to be appropriate by one skilled in the art. It is expected that the dosages will vary, depending upon the pharmacokinetic and pharmacodynamic characteristics of the particular agent, and its mode and route of administration, as well as the age, weight, and health (including renal and hepatic function) of the recipient; the nature and extent of the disease; the frequency and duration of the treatment; the type of, if any, concurrent therapy; and the desired effect. It is expected that a useful dosage contains between about 0.1 to 300 mg of active ingredient per kilogram of body weight. Ordinarily, 1 to 100 mg, and preferably 10 to 50 mg of active ingredient (nucleic acid or protein) per kilogram of body weight per day, given in divided doses or in sustained release form, is appropriate.

The therapeutic compositions of the invention may be administered to a patient by any appropriate mode, e.g., orally, parenterally, intraperitoneally, or intravenously, as determined by one skilled in the art. Alternatively, it may be desired to administer the treatment surgically to the target tissue, e.g., during angioplasty. The treatments of the invention may be repeated as needed, as determined by one skilled in the art.

Therapeutic or prophylactic effectiveness of the present fusion proteins in treating the above-described illnesses or any other illnesses can be assessed using animal models for the illnesses, as described in the examples below.

In addition to treating illnesses, the fusion proteins of the invention can be used in vitro. For instance, the fusion proteins are capable of preventing platelet aggregation and degranulation, and can therefore be used in preserving platelets in blood banking, e.g., cryopreservation of platelets at temperatures that inhibit growth of microorganisms, generally 4° C.–15° C. To do this, an appropriate amount of a fusion protein of the invention (e.g., calpastat at about 1–100 μM) can be added to platelet preparations. The fusion proteins can also be used to facilitate transfusion of autologous blood from sickle cell patients and patients with sickle trait by preventing irreversible sickling during blood storage. Thus, the fusion proteins of the invention can be used in conjunction with storage at low temperature and other techniques for promoting successful storage of blood from sickle cell patients or patients with sickle trait (Asakura et al., *Blood Cells, Molecules & Diseases* 22:297–306, 1996; Vichinsky et al., *New Engl. J. Med.* 322:1617–1621, 1990).

The fusion proteins of the invention offer several advantages as inhibitors of calpains. For instance, they are expected to be reversible in its activity, since the interaction of calpastatin peptides with calpain is reversible (see, e.g., Anagli et al., *European J. Biochem.* 241:948–954, 1996). Moreover, the presence of a signal sequence allows the fusion proteins to easily enter cells.

Described below are examples which demonstrate that calpastat, which is pharmacologically active at concentrations ranging from about 1 to about 100 μM, (i) prevents platelet aggregation and degranulation; (ii) inhibits erythrocyte sickling; and (iii) inhibits $Ca^{2+}$-mediated activation of HIV-1 provirus. These specific examples entail the use of calpastat; other fusion proteins of the invention can be used in a similar manner. Additional examples describe protocols useful in optimizing the therapeutic effectiveness of the new fusion proteins in animal models.

The examples are meant to illustrate the methods and materials of the present invention. Suitable modifications and adaptations of the variety of conditions and parameters which are obvious to those skilled in the art are within the spirit and scope of the present invention.

EXAMPLE 1
Inhibition of Platelet Aggregation

The experiment described below demonstrates that calpastat, but not a mutant of calpastat (S-TIPPEY-ala), effectively inhibits platelet aggregation.

Platelets used in this study were purified from serum on a SEPHAROSE 2B column in PIPES buffered saline containing glucose. After a pre-incubation with 45 μM calpastat or S-TIPPEY-ala for 30 minutes at 37° C., the platelets were placed in a cuvette in a BIODATA aggregometer, which measures turbidity of the solution by nephlometry (light scatter). Aggregation was induced with thrombin (0.1 to 1 unit/ml) or the thrombin receptor agonist peptide SFLLR (SEQ ID NO:5). Calpastat inhibited platelet aggregation, with maximal inhibition achieved at 45 μM calpastat. In contrast, S-TIPPEY-ala had no activity. A version of S-TIPPEYIN lacking the signal sequence similarly had no activity.

This result demonstrates that calpastat can effectively inhibit platelet aggregation and that the seven conserved amino acids mutated in S-TIPPEY-ala are essential for calpastatin function. This result also demonstrates that the platelet inhibitory activity of calpastat lies in the calpastatin portion of calpastat, not the amino-terminal kFGF signal sequence which makes it cell-penetrating.

EXAMPLE 2
Inhibition of α-Granule Secretion

In order to determine if S-TIPPEYIN inhibits α-granule secretion in platelets, surface expression of P-selectin, which is an indication of α-granule secretion, was induced with SFLLR (SEQ ID NO:5) and analyzed by flow cytometry using an antibody against P-selectin. In these experiments, blood from healthy volunteers was collected into sodium citrate (4% w/v) and centrifuged at 200×g for 10 minutes to prepare platelet-rich plasma ("PRP"). Platelets were subsequently purified from PRP by gel filtration using a SEPHAROSE 2B column in PIPES buffer. Twenty μl of platelets (approximately $2\times10^8$ platelets/ml) were aliquoted into eppendorf tubes. One μl of S-TIPPEYIN, ZLLY (i.e., Cbz-LLYCHN$_2$; Crawford et al., *Biochem. J.* 248:579–588, 1988), or S-TIPPEY-ala was added to a final concentration of 6.25, 12.5, 25, 50, or 100 μM. The platelets were then incubated for 2 hours at 37° C. Subsequent to the incubation, platelets were exposed to either 1 μl PBS (unstimulated) or 1 μl of SFLLR (SEQ ID NO:5; stimulated) at the indicated concentration. After 30 seconds, a 7.5 μl aliquot was transferred to an eppendorf tube containing non-immune serum the antibodies in which were conjugated to phycoerythrin. Platelets were incubated with antibodies for 20 minutes at room temperature. The mixture was subsequently diluted with 1 ml of paraformaldehyde 2% and incubated at 4° C. for 2 hours. Antibody binding to platelet surface P-selectin was quantified using a FACSCAN flow cytometer (Becton Dickerson, San Jose, Calif.). Results were reported as the geometric mean of the relative fluorescence.

Figure 2:
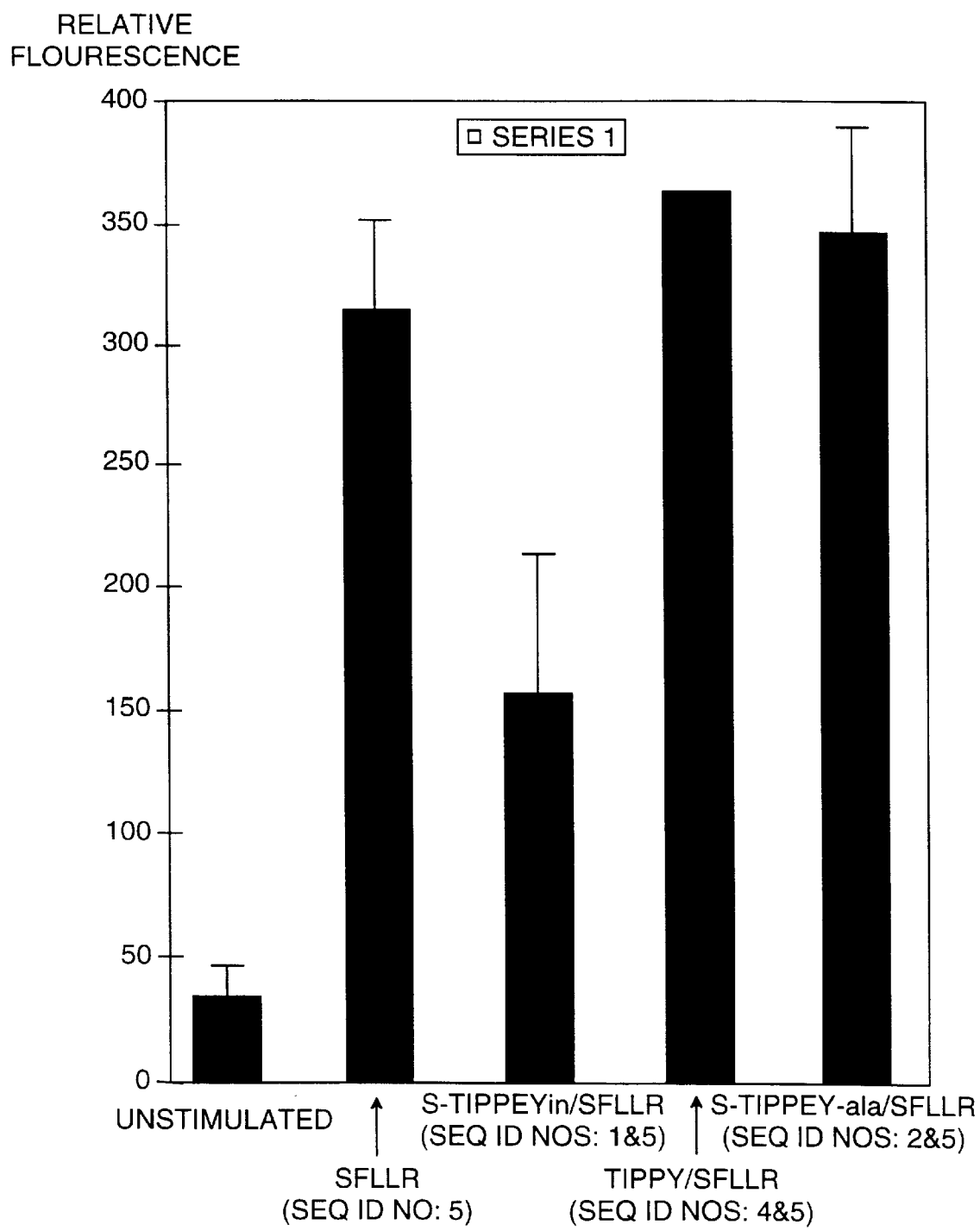
FIG. 2 is a bar graph comparing the extents of inhibition of P-selectin surface expression by S-TIPPEYIN, TIPPEY (i.e., the calpastatin peptide portion of S-TIPPEYIN), and S-TIPPEY-ala.

As demonstrated in FIG. 2, stimulation of gel-filtered platelets with SFLLR (50 μM) results in an approximately 10-fold increase in surface P-selectin expression (compare the bars marked respectively "unstimulated" and "SFLLR"). Pre-incubation with S-TIPPEYIN resulted in only a 5-fold increase in P-selectin surface expression (compare the bars marked respectively "unstimulated" and "S-TIPPEYIN/SFLLR"). In contrast, pre-incubation with TIPPEY, a corresponding peptide lacking the KFGF signal sequence, had little effect on SFLLR-induced P-selectin surface expression (see the bar marked "TIPPEY/SFLLR"). Similarly, a peptide in which the seven conserved residues of calpastat were mutated to alanine had no effect on SFLLR-induced P-selectin surface expression (see the bar marked "S-TIPPEY-ala/SFLLR").

Figure 3:
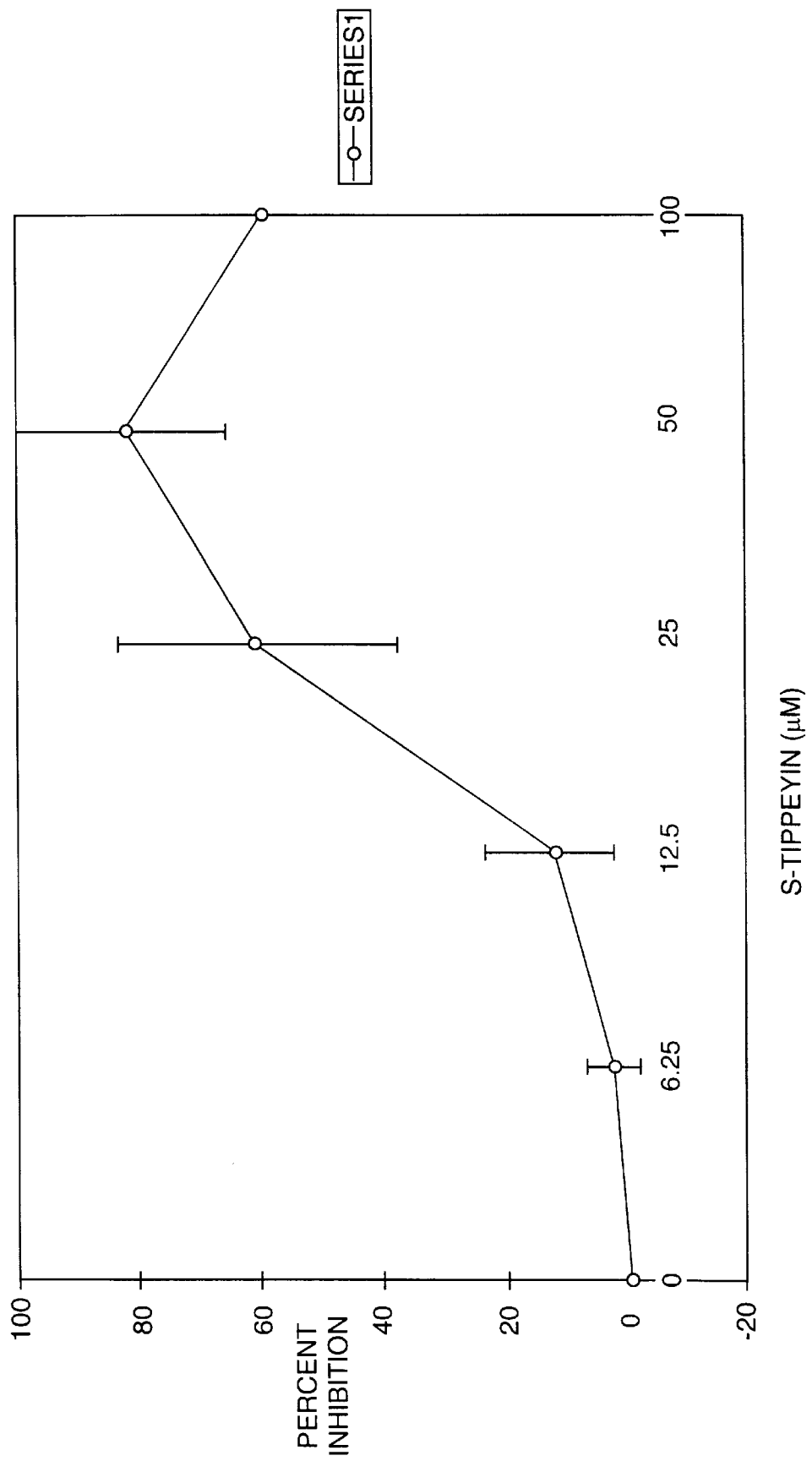
FIG. 3 is a graph showing the dose-dependent inhibition of P-selectin surface expression by S-TIPPEYIN.

The inhibitory effect of S-TIPPEYIN did not result from inhibition of the P-selectin antibody by surface P-selectin, since incubation of platelets with S-TIPPEYIN following exposure to SFLLR (SEQ ID NO:5) had no effect on the binding of antibody to surface expressed P-selectin. As indicated in FIG. 3, S-TIPPEYIN inhibits the surface expression of P-selectin in a dose-dependent manner. Half-maximal inhibition occurred at about 15–20 μM, and maximal-inhibition occurred at about 40–60 μM.

S-TIPPEYIN also inhibited P-selectin surface expression induced by ionophore A23187.

EXAMPLE 3
Inhibition of Ionophore-Dependent Calpain Degradation of Two Substrates in Platelets To investigate whether calpastat inhibits calpain activity in platelets, the ionophore-dependent proteolysis of actin binding protein (ABP; about 280 kD) and talin (about 240 kD), both of which are substrates of both μ- and m-calpains, was examined.

To do so, platelets were pre-incubated with ZLLY-CHN$_2$, DMSO (solvent for ZLLY-CHN$_2$), calpastat, or HEPES buffer (buffer for calpastat), and then treated with or without ionophore A23187 for 5, 8 or 10 minutes. The platelets were then gel-purified as described above. Whole cell lysates were prepared and fractionated by SDS polyacrylamide gel electrophoresis. The data showed that both ZLLY-CHN$_2$ and calpastat inhibited A23187-dependent calpain degradation of ABP and talin in platelets at all three time points examined. Nonetheless, only calpastat inhibited platelet aggregation and secretion.

EXAMPLE 4
Delay of Hypoxia-Induced Sickling of Sickle Erythrocytes and Inhibition of Irreversible Sickling Calpastat was examined for its ability to inhibit sickling of red blood cells isolated from sickle cell patients. S-TIPPEY-ala, which demonstrates no inhibition of purified μ-calpain, was used as a control peptide.

To examine sickling, a wet preparation of red blood cells (as opposed to a dried smear) was made by placing blood under a coverslip on a glass slide. The slide was placed under a light microscope, and the number of cells displaying sickled morphology was counted. $Na_2S_2O_5$ was used to increase the rate of sickling.

Figure 4:
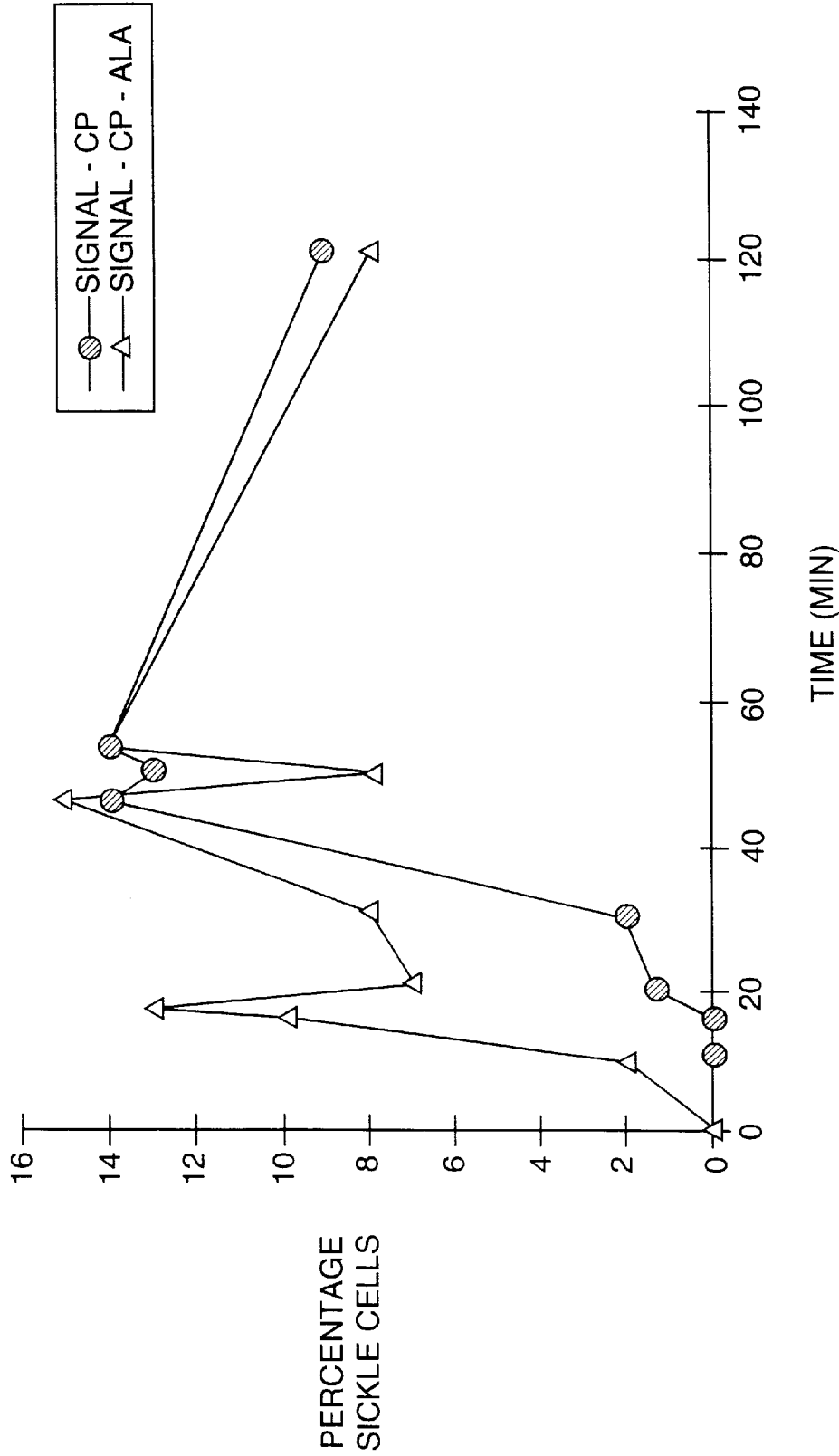
FIG. 4 is a graph showing the time course of $Na_2S_2O_5$-induced erythrocyte sickling in the presence of calpastat (marked "signal-CP") or S-TIPPEY-ala (marked "signal-CP-ala").

When EDTA-anticoagulated peripheral blood from a sickle cell patient was preincubated with calpastat for 10 minutes prior to exposure to sodium metabisulfite ($Na_2S_2O_5$), there was a significant delay (about 30 minutes) in sickling. The time course of sickling is shown in FIG. 4 for this patient. There was no detectable difference in the final percentage of sickled cells.

Figure 5:
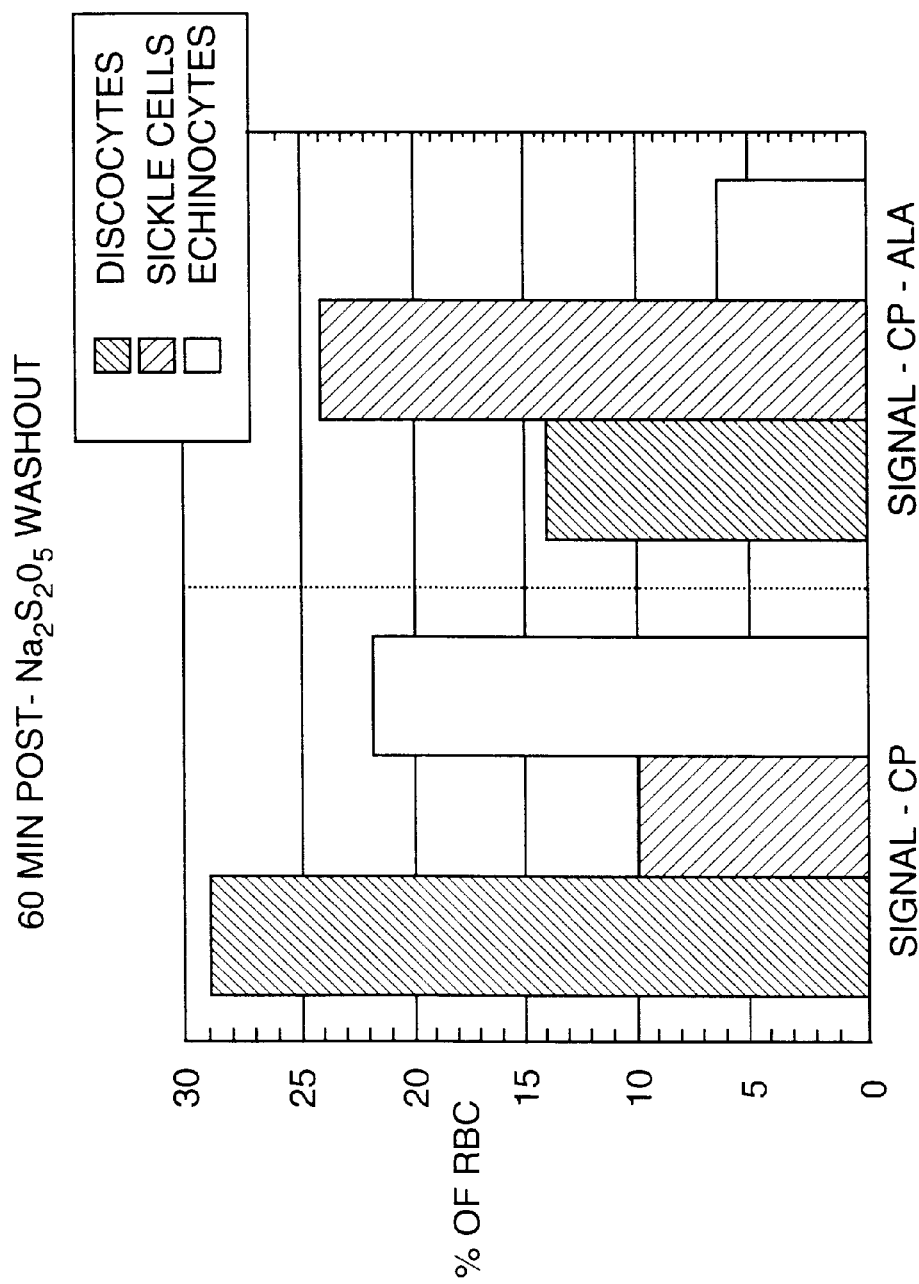
FIG. 5 is a bar graph showing the percentages of discocytes, sickle cells, and echinocytes at 60 min following removal of $Na_2S_2O_5$. The erythrocytes (i.e., RBC) were pre-treated with calpastat (marked "signal-CP") or S-TIPPEY-ala (marked "signal-CP-ala").

In a second experiment, the effect of calpastat on recovery from sickling was measured. Blood from the same patient was incubated with $Na_2S_2O_5$ for two hours in a microfuge tube. The supernatant plasma was then removed from the settled erythrocytes and the erythrocytes were diluted in four volumes of saline. The washed erythrocytes were then incubated in saline, and Wright-Giemsa stained smears were made at 60 minutes following the washout of $Na_2S_2O_5$. The percentage of sickled cells in the microfuge tube preparation was found to be at least 2-fold greater than in the microscope slide preparation. At 60 minutes following the $Na_2S_2O_5$ washout, the percentage of discocytes was two-fold greater and the percentage of sickled cells two-fold lower in calpastat-treated cells as compared to S-TIPPEY-ala-treated cells. The percentages of discocytes, sickled cells and echinocytes are shown in FIG. 5.

These observations suggest that calpastat delays the onset of sickling in erythrocytes and facilitates the recovery of discocytes following sickling in vitro.

EXAMPLE 5
Inhibition of HIV Provirus Activation

Thapsigargin ("Tpg"), an inhibitor of the $Ca^{2+}$-dependent ATPase, has been demonstrated to induce intracellular $Ca^{2+}$ leakage and activation of HIV-1 proviral transcription and virion release. Calpastat was examined for its ability to inhibit thapsigargin-induced HIV-1 activation in U1 promonocytes.

U1 is a human promonocytic cell line that is chronically infected with HIV-1 and that constitutively expresses low levels of HIV-1. U1 cells are derived from U937 cells, which are acutely infected with HIV-1, and possess two integrated copies of HIV-1 pro-viral DNA. In the present experiment, $1 \times 10^6$ cells/ml were treated with various dosages of calpastat and incubated for one hour at 37° C. After the incubation, various concentrations of Tpg were added to the calpastat-treated cells and were aliquoted into a 24-well plate. To observe the stimulation of HIV-1 activity by Tpg, equivalent numbers of cells were treated with Tpg alone. The cells were then incubated at 37° C. for up to 4 days, and supernatants from the cell culture were collected each day to measure HIV-1 activity. The viability of cells treated with both Tpg and calpastat were determined each day by Trypan-blue exclusion test. The HIV-1 activity in the collected supernatants was determined by measuring the HIV-1 p24 core antigen protein by ELISA (Dupont Medical Products, Boston, Mass.) according to the manufacturer's instructions.

Figure 6:
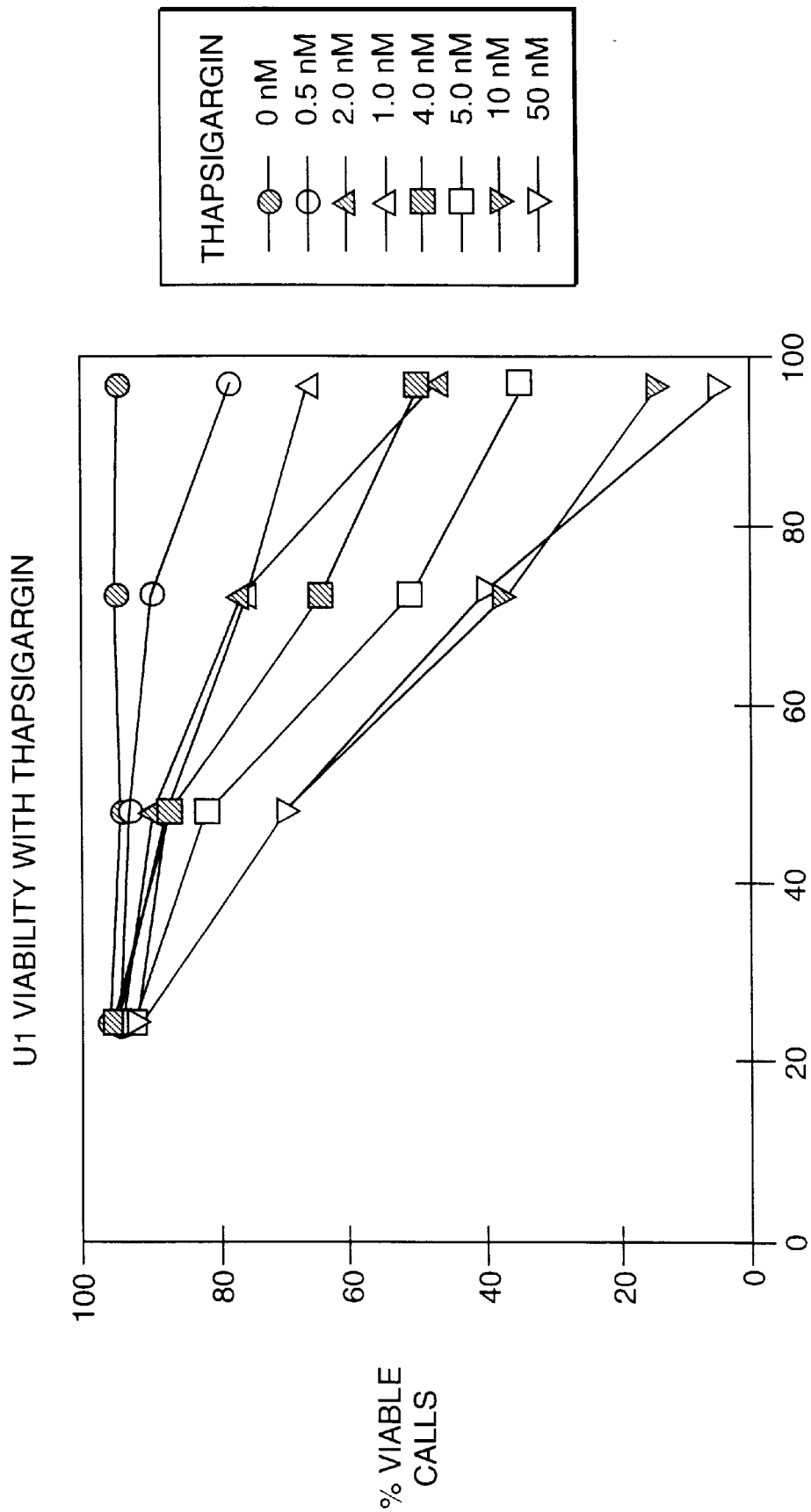
FIG. 6 is a graph showing the time course of the viability of U1 cells treated with the indicated concentrations of thapsigargin.
Figure 7A:
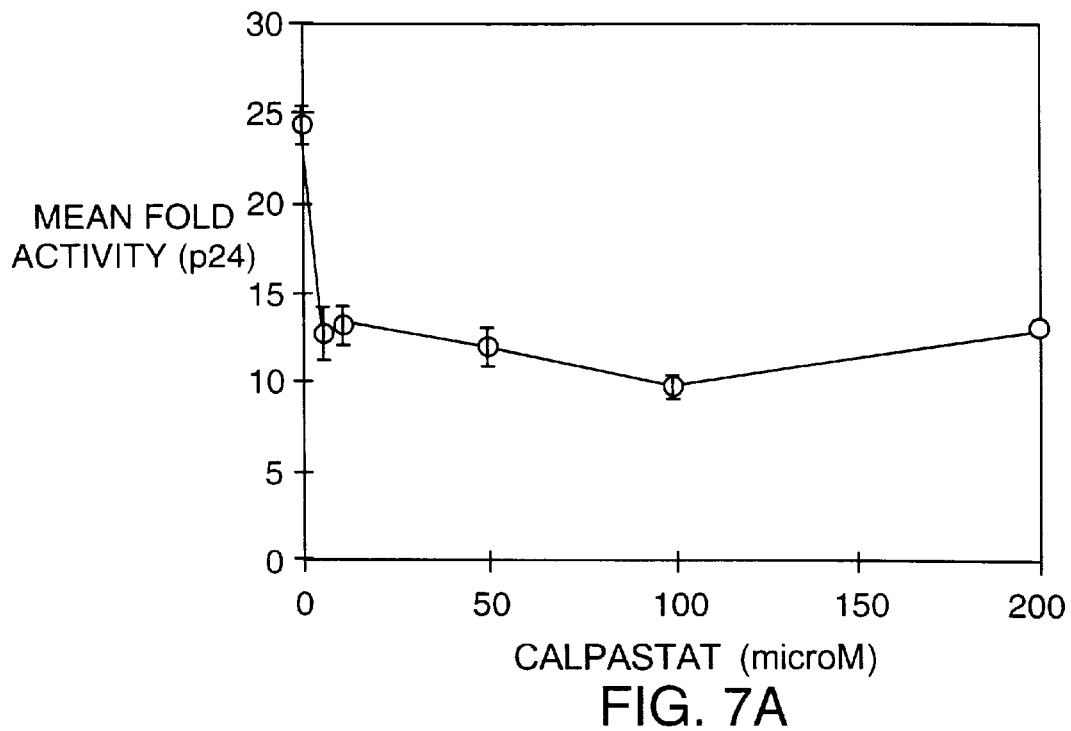
FIGS. 7A–7D are graphs showing the production of HIV p24 antigen (indicated by "mean fold activity") in U1 cells treated with various concentrations of calpastat. The mean fold activity was recorded at 24 (A), 48 (B), 72 (C), or 96 (D) hr following thapsigargin induction.
Figure 7B:
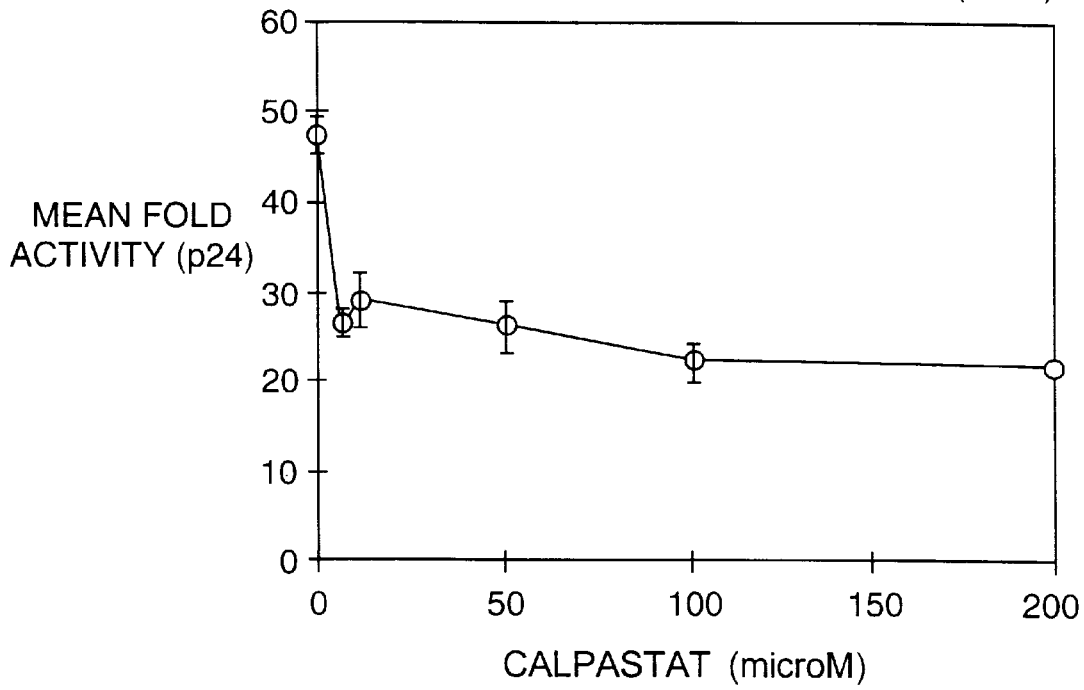
Figure 7C:
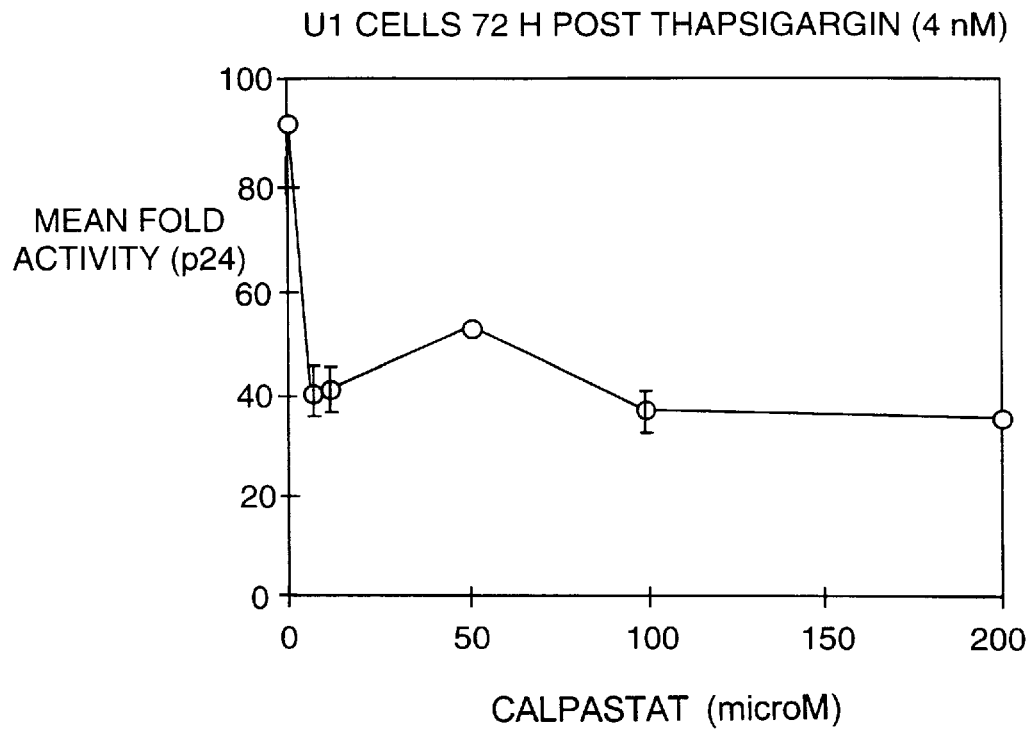
Figure 7D:
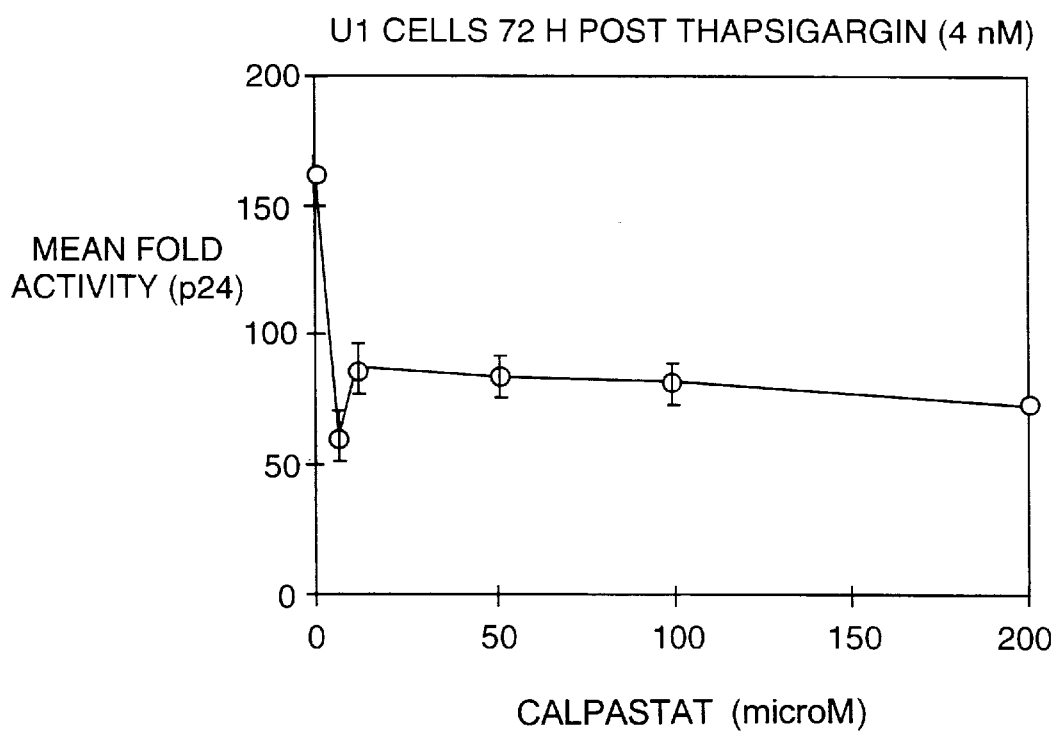

The data showed that Tpg-induced activation of HIV-1 occurred over a narrow concentration range, with minimal induction at 1 nM (1.37-fold induction of virus at 24 h) and maximal induction at 5 nM (20-fold induction at 24 h). Increasing doses of Tpg correlated with decreasing cell viability after 24 hours of incubation (FIG. 6). For instance, U1 cell viabilities at 96 hr were about 50% and 5% in the presence of 4.0 and 50 nM Tpg, respectively.

Five μM calpastat decreased mean fold viral production by 47, 44, 55 and 61% at 24, 46, 72 and 96 hours of Tpg stimulation, respectively (FIGS. 7A–7D). These results were highly statistically significant, and indicated that calpastat inhibits HIV-1 release from infected cells by about 50%.

Figure 8:
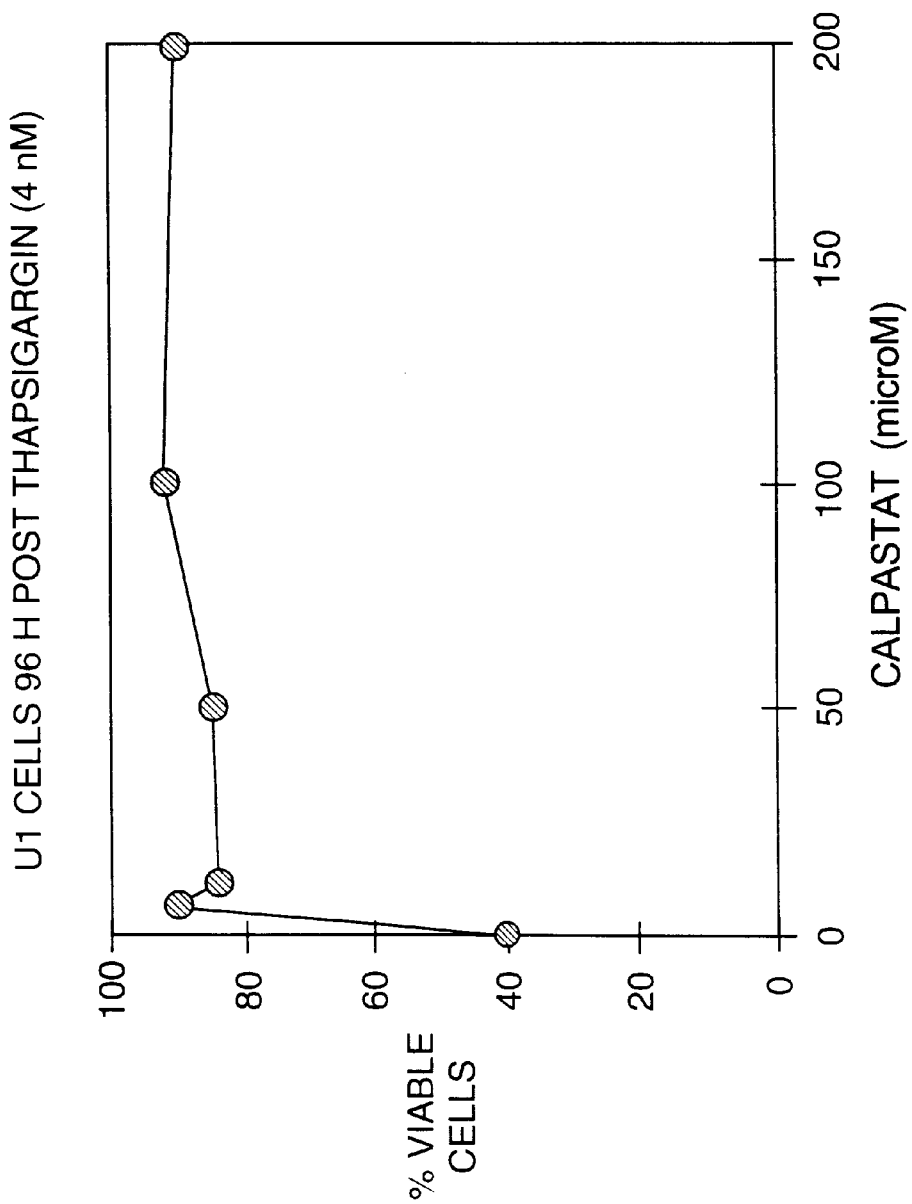
FIG. 8 is a graph showing the percentage of viable cells treated with various concentrations of calpastat at 96 hr following thapsigargin induction.

U1 viability studies confirmed that inhibition of HIV-1 activation correlates with increase in cell viability. Calpastat, at a concentration of 5 μM, was shown to increase the viability of U1 cells in 4 nM Tpg from 40% to 90% at 96 hr (FIG. 8). This result demonstrates that calpastat prevents cell death caused by HIV-1 activation.

EXAMPLE 6
Inhibition of Calpain Activity

To assess the ability of calpastat to inhibit calpain activity, a fluorometric calpain assay was performed. The assay determined specific peptidyl hydrolysis of the peptidyl 7-amino bond of suc-LLVY-AMC (SEQ ID NO:7) by calpain.

Figure 9:
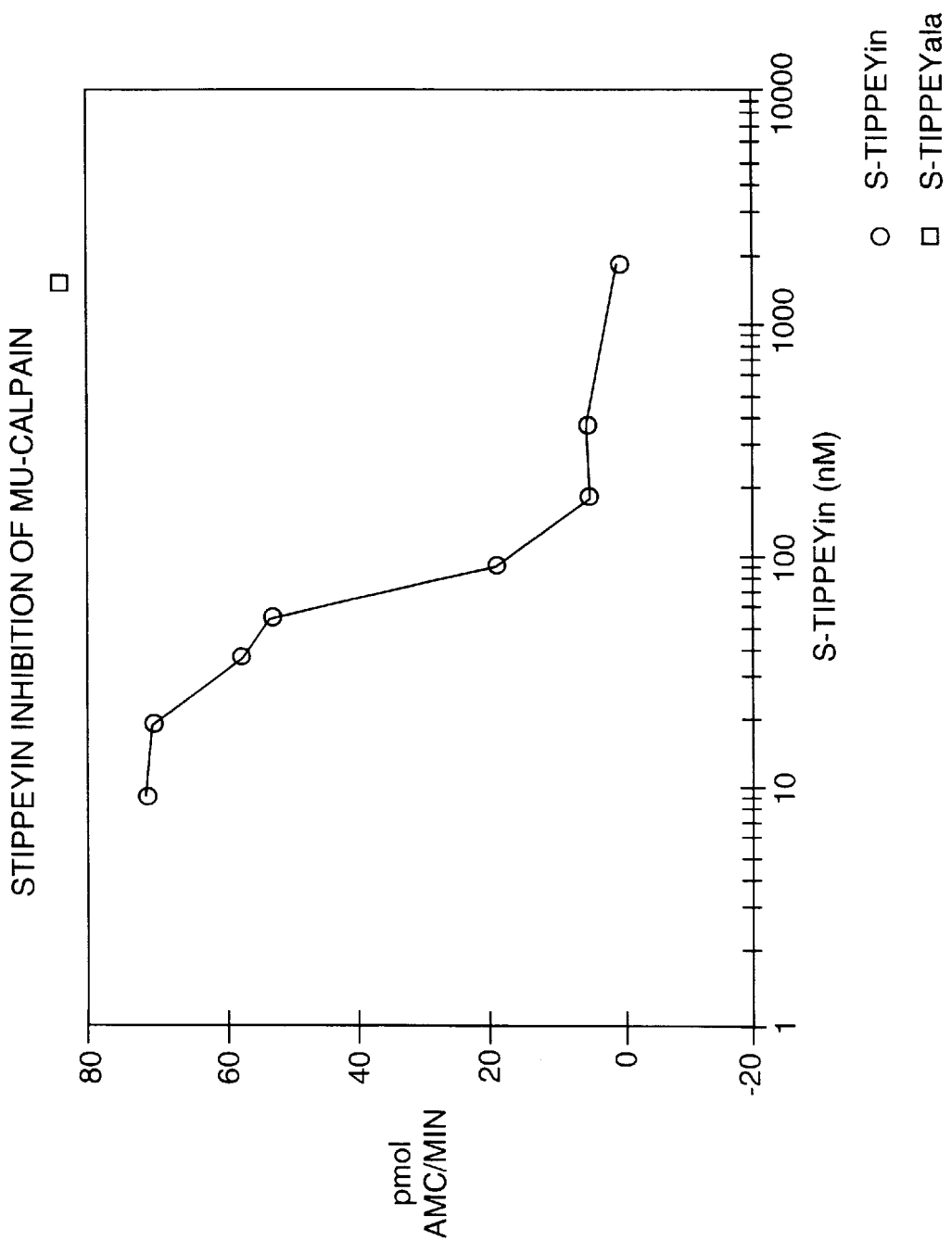
FIG. 9 is a graph showing the dose-dependent inhibition of $\mu$-calpain by S-TIPPEYIN. S-TIPPEY-ala was used as a negative control. Suc-LLVY-AMC (SEQ ID NO:7) was used as a calpain substrate.

The assay was done in a 0.5 ml reaction volume at 37° C. The reaction buffer contained 50 mM KCl, 10 mM Tris-HCl (pH 7.5), 1 mM EDTA, and 1 mM DTT. Two hundred μM suc-LLVY-AMC (SEQ ID NO:7) was added along with 5 mM $CaCl_2$. Calpastat or S-TIPPEY-ala was then added at the given concentrations (FIG. 9). At time zero, 4.0 μg of purified μ-calpain was added, resulting in a final concentration of 70 nM enzyme. The initial rate of AMC production was measured by fluorimetry for the first few minutes. Fluorescent excitation was at 360±2 nm and emission detection was at 460±10 nm. AMC standard solutions were used to determine moles of AMC generated from emission data. The initial rate of substrate cleavage was given as picomoles of AMC released/microgram calpain/minute.

This assay showed that calpastat inhibits μ-calpain cleavage of suc-LLVY-AMC (SEQ ID NO:7) with an $IC_{50}$ of 50 nM (FIG. 9). In contrast, S-TIPPEY-ala had no inhibitory activity in this assay even at a concentration of 10 μM.

Figure 10:
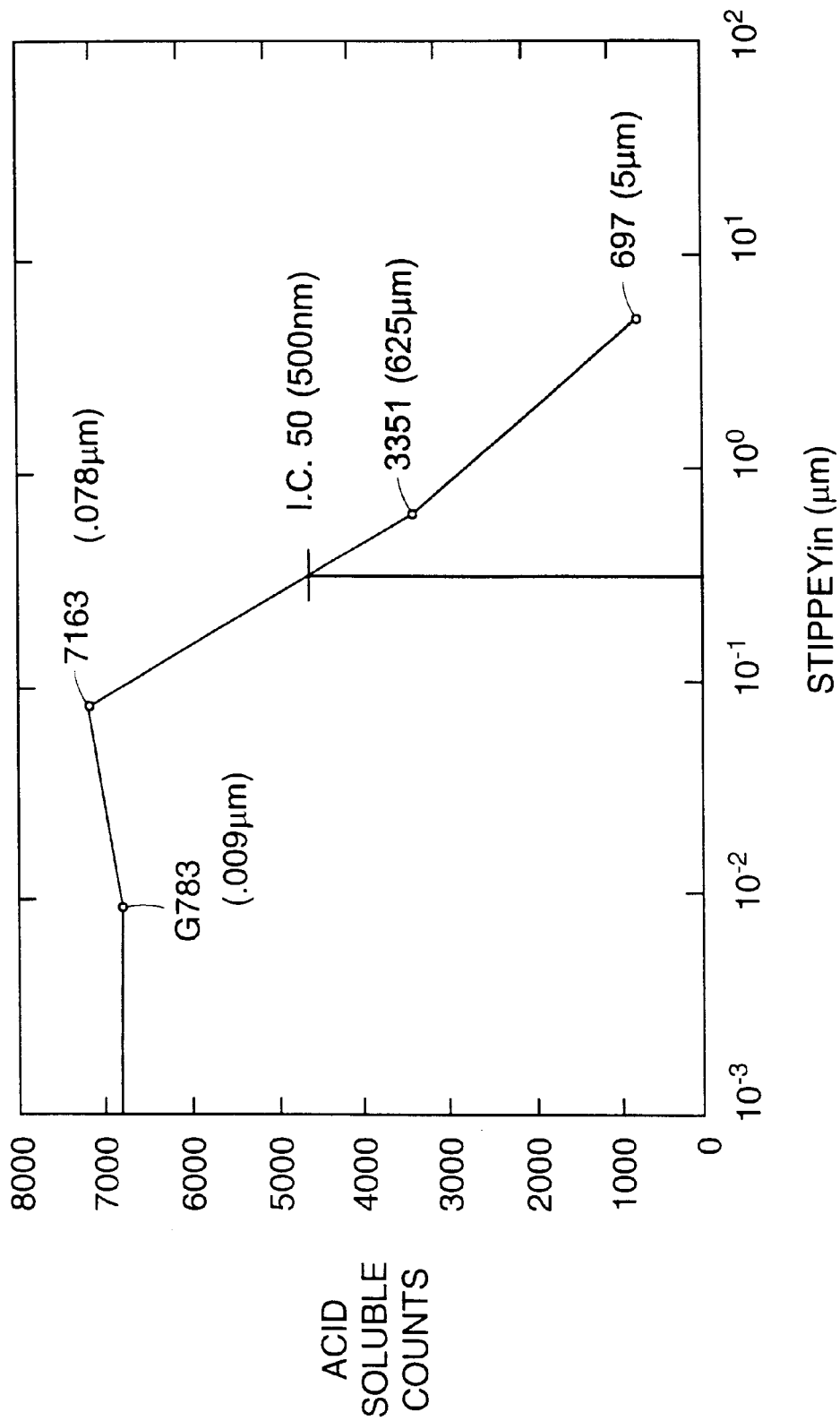
FIG. 10 is a graph showing the dose-dependent inhibition of $\mu$-calpain by S-TIPPEYIN. [$^{14}$C]-methylcasein was used as a calpain substrate.

Another calpain inhibition assay entails measurement of the inhibition of calpain cleavage of a protein substrate methylcasein in a cell-free system. Methylcasein is a substrate of both μ- and m-calpain (see, e.g., DeMartino et al., J. Biol. Chem. 261:12047–12052, 1986; Croall et al., Physiol. Rev. 71:813–847, 1991). The assay was done in a 0.1 ml reaction volume at 30° C. The reaction buffer contained 50 mM MOPS (pH 7.5) and 1.4 mM DTT. The substrate was added, along with 10 mM $Ca^{2+}$, to a final concentration of 0.5 mg/ml. Calpastat or S-TIPPEY-ala was added at the given concentrations (FIG. 10). Purified μ-calpain was then added to the reaction mix to give a concentration of 2.7 μM. The reaction was allowed to proceed for 10 minutes, and was stopped with 0.7 ml of 10% tricholoracetic acid containing 2 mg/ml bovine serum albumin. The reaction mix was then incubated on ice for 1 hour, and centrifuged at 1,500×g for 10 minutes. Two hundred μl of the supernatant was counted for $^{14}C$ cpm in 5 ml of scintillation fluid. Calpain activity was determined by subtracting $Ca^{2+}$-independent acid soluble cpm (in the presence of EDTA) from $Ca^{2+}$-dependent acid soluble cpm (in the presence of excess $Ca^{2+}$) The $IC_{50}$ of calpastat in this assay was 500 nM.

EXAMPLE 7
Cerebral Ischemia in Rats

This example provides a protocol for determining the effectiveness of a fusion protein of the invention in reducing cerebral infarction in rats that have undergone ischemia surgery.

Experimental rats are anesthetized with chloral hydrate prior to surgery. Rectal temperature is maintained at 37±0.5° C. using a heating blanket connected to a temperature feedback monitor. The right femoral artery is cannulated with a silicon catheter for measurement of blood pressure and blood gases, and to obtain samples for determination of the fusion protein level in serum. The right femoral vein is similarly cannulated for infusions.

For ischemia surgery, a 4-0 nylon suture with a flame-rounded tip is inserted into the right external carotid artery just distal to the right common carotid bifurcation and advanced 18.5–19.5 mm (depending on the animal's weight) through the internal/intracranial carotid arteries until the tip occluded the origin of the MCA. The suture is left in place for 2 hours and then withdrawn into the external carotid artery. Immediately following restoration of blood flow, animals are continuously infused for 3 hours with either saline (0.5 ml/hr), a fusion protein of the invention or a control peptide. Arterial blood gases, pH, and hematocrit are monitored before vascular occlusion and at the end of drug infusion. Mean arterial blood pressure is measured before and during occlusion and throughout drug infusion. Blood samples for determination of the fusion protein serum levels (e.g., by Western blotting) are drawn 2.5 hours after the start of drug infusion and 30 minutes following drug termination.

To measure the extent of infarction, the rats are sacrificed 48 hours after the onset of occlusion and cerebral infarct volume is determined by computer image analysis of coronal brain slices stained with 2% 2,3,5-triphenyltetrazolium chloride (BIOQUANT, R+M Biometrics, Nashville Tenn.). Infarct volume is calculated using the "indirect" method, in which the infarcted area of a brain slice is first determined by subtracting the undamaged area of ipsilateral hemisphere from the total area of the contralateral hemisphere (Swanson et al., *J. Cereb. Blood Flow Metab.* 10:290–293, 1990). The infarcted area is then multiplied by section thickness (2 mm) to obtain infarct volume for that slice. Total brain infarct volume is finally obtained by summing the volumes of the series of 7 brain slices prepared from each animal. Statistical analysis of treatment groups is performed using one-way ANOVA followed by a two-tailed unpaired t-test.

EXAMPLE 8
Treatment of Alzheimer's Disease

The fusion proteins of the invention may be useful for treatment of Alzheimer's disease. Fusion proteins can be tested using a murine model of Alzheimer's disease (see, e.g., Games et al., *Nature* 373:523–27, 1995; Sisk et al., *J. Neurosci.* 16:5795–5811, 1996; Irizarry et al., *J. Neurosci.* 17:7053, 1997; Johnson-Wood et al., *Proc. Natl. Acad. Sci. USA* 94:1550–55, 1997).

EXAMPLE 9
Treatment of Cataracts

The fusion proteins of the invention may be useful in treatment of cataracts. The fusion proteins can be screened for effectiveness using animal models of cataract disease (see, e.g., Zigler, *Exp. Eye Res.* 50:651–7, 1990; Shearer et al., *Current Eye Res.* 6:289–300, 1987).

EXAMPLE 10
Treatment of Sickle Crisis

The fusion proteins of the invention may be useful in treatment of sickle crisis. The fusion proteins can be screened for effectiveness using animal models of sickle cell disease (see, e.g., Ryan et al., *Science* 278:873–876, 1997; Pászty et al., *Science* 278:876–878, 1997).

Other Embodiments

It is to be understood that while the invention has been described in conjunction with the detailed description thereof, that the foregoing description is intended to illustrate and not limit the scope of the invention, which is defined by the scope of the appended claims. For example, the fusion proteins may be used to inhibit activation of NF-κB regulated viruses, e.g., cytomegaloviruses, hepatitis B virus, herpes viruses, adenoviruses, HTLV-I, Sendai virus, human herpes virus 6, and HSV type 1 (see, e.g., Baeuerle, *Biochem. Biophys. ACTA* 1072:63–80, 1991).

Other aspects, advantages, and modifications are within the scope of the following claims.

We claim:

1. A method of inhibiting a calpain in a cell, comprising contacting the cell with an effective amount of a fusion protein having a first portion and a second portion, the first portion comprising a signal sequence capable of delivering the fusion protein into the cell, the second portion comprising the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18);
wherein:
   Xaa at position 1 is Glu, Asp, or Lys;
   Xaa at position 2 is Lys, Glu, Ala, or Asn;
   Xaa at position 5 is Glu, Lys, or Ile;
   Xaa at position 6 is Arg, Lys, or Asp;
   Xaa at position 7 is Asp, or Glu;
   Xaa at position 8 is Asp, Val, Ser, Gly, or Glu;
   Xaa at position 13 is Glu, Lys, or Asp;
   Xaa at position 15 is Arg, Lys, or Gln;
   Xaa at position 16 is Glu, His, Lys, or Leu; and
   Xaa at position 19 is Glu, Asp, Asn, Ala, or Val.

2. The method of claim 1, wherein the amino-terminal end of the second portion is covalently bonded to the carboxy-terminal end of the first portion by a peptide bond.

3. The method of claim 2, wherein the second portion has the sequence of SEQ ID NO:4.

4. The method of claim 2, wherein the first portion has the sequence of SEQ ID NO:3.

5. The method of claim 2, wherein the fusion protein has the sequence of SEQ ID NO:1.

6. The method of claim 1, wherein the cell is a platelet.

7. The method of claim 1, wherein the cell is a sickle erythrocyte.

8. The method of claim 1, wherein the cell is an HIV-infected cell.

9. A method of preventing platelet aggregation, comprising contacting a plurality of platelets with an effective amount of a fusion protein comprising a first portion and a second portion, the first portion comprising a signal sequence capable of delivering the fusion protein into the cell, the second portion comprising the sequence Xaa-Xaa- Leu-Gly-Xaa-Xaa-Xaa-Xaa-Thr-Ile-Pro-Pro-Xaa-Tyr-Xaa-Xaa-Leu-Leu-Xaa (SEQ ID NO:18);
wherein:
   Xaa at position 1 is Glu, Asp, or Lys,
   Xaa at position 2 is Lys, Glu, Ala, or Asn;
   Xaa at position 5 is Glu, Lys, or Ile;
   Xaa at position 6 is Arg, Lys, or AsD;
   Xaa at position 7 is Asp, or Glu;
   Xaa at position 8 is Asp, Val, Ser, Gly, or Glu;
   Xaa at position 13 is Glu, Lys, or Asp;
   Xaa at position 15 is Arg, Lys, or Gln;
   Xaa at position 16 is Glu, His, Lys, or Leu; and
   Xaa at position 19 is Glu, Asµ, Asn, Ala, or Val.

10. A method of preventing platelet degranulation, comprising contacting a plurality of platelets with an effective amount of a fusion protein comprising a first portion and a second portion, the first portion comprising a signal sequence capable of delivering the fusion protein into the cell, the second portion comprising the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18);
wherein:
   Xaa at position 1 is Glu, Asp or Lys;
   Xaa at position 2 is Lys, Glu, Ala, or Asn;
   Xaa at position 5 is Glu, Lys, or Ile;
   Xaa at position 6 is Arg, Lys, or Assp;
   Xaa at position 7 is Asp, or Glu;
   Xaa at position 8 is Asp, Val, Ser, Gly, or Glu;
   Xaa at position 13 is Glu, Lys, or Asp;
   Xaa at position 15 is Arg, Lys, or Gln;
   Xaa at position 16 is Glu, His, Lys, or Leu; and
   Xaa at position 19 is Glu, Asp, Asn, Ala, or Val.

11. A method of inhibiting erythrocyte sickling, comprising contacting a sickle erythrocyte with an effective amount of a fusion protein comprising a first portion and a second portion, the first portion comprising a signal sequence capable of delivering the fusion protein into the cell, the second portion comprising the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18);
wherein:
   Xaa at position 1 is Glu, Asp, or Lys;
   Xaa at position 2 is Lys, Glu, Ala, or Asn;
   Xaa at position 5 is Glu, Lys, or Ile;
   Xaa at position 6 is Arg, Lys, or Asp,
   Xaa at position 7 is Asd, or Glu;
   Xaa at position 8 is Asp, Val, Ser, Gly, or Glu;
   Xaa at position 13 is Glu, Lys, or Asp;
   Xaa at position 15 is Arg, Lys, or Gln;
   Xaa at position 16 is Glu, His, Lys, or Leu; and
   Xaa at position 19 is Glu, Asp, Asn, Ala, or Val.

12. A method of inhibiting activation of HIV provirus, comprising contacting an HIV-infected cell with an effective amount of a fusion protein comprising a first portion and a second portion, the first portion comprising a signal sequence capable of delivering the fusion protein into the cell, the second portion comprising the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18);
wherein:
   Xaa at position 1 is Glu, Asp , or Lys;
   Xaa at position 2 is Lys, Glu, Ala, or Asn;
   Xaa at position 5 is Glu, Lys, or Ile;
   Xaa at position 6 is Arg, Lys, or Asp;
   Xaa at position 7 is Asp, or Glu;
   Xaa at position 8 is Asp, Val, Ser, Gly, or Glu;
   Xaa at Position 13 is Glu, Lys, or Asp;
   Xaa at position 15 is Arg, Lys, or Gln;
   Xaa at position 16 is Glu, His, Lys, or Leu; and
   Xaa at position 19 is Glu, Asp, Asn, Ala, or Val.

13. The method of any of claims 9–12, wherein the amino-terminal end of the second portion is covalently bonded to the carboxy-terminal end of the first portion by a peptide bond.

14. The method of any of claims 9–12, wherein the second portion has the sequence of SEQ ID NO:4.

15. The method of any of claims 9–12, wherein the first portion has the sequence of SEQ ID NO:3.

16. The method of any of claims 9–12, wherein the fusion protein has the sequence of SEQ ID NO:1.

17. A fusion protein comprising a first portion and a second portion, the first portion comprising a signal sequence capable of delivering the fusion protein into a eukarvotic cell, the second portion comprising the sequence Xaa-Xaa-Leu-Gly-Xaa-Xaa-Xaa-Xaa-Thr-Ile-Pro-Pro-Xaa-Tyr-Xaa-Xaa-Leu-Leu-Xaa (SEQ ID NO:18);
wherein:
   Xaa at position 1 is Glu, Asp, or Lys;
   Xaa at position 2 is Lys, Glu, Ala, or Asn;
   Xaa at position 5 is Glu, Lys, or Ile;
   Xaa at position 6 is Arg, Lys, or Asp;
   Xaa at position 7 is Asp, or Glu;
   Xaa at position 8 is Asp, Val, Ser, Gly, or Glu;
   Xaa at position 13 is Glu, Lys, or Asp;
   Xaa at position 15 is Arg, Lys, or Gln;
   Xaa at position 16 is Glu, His, Lys, or Leu; and
   Xaa at position 19 is Glu, Asp, Asn, Ala, or Val.

18. The fusion protein of claim 17, wherein the amino-terminal end of the second portion is covalently bonded to the carboxy-terminal end of the first portion by a peptide bond.

19. The fusion protein of claim 18, wherein the second portion has the sequence of SEQ ID NO:4.

20. The fusion protein of claim 18, wherein the first portion has the sequence of SEQ ID NO:3.

21. A protein having the sequence of SEQ ID NO:1.

22. The fusion protein of claim 17 wherein the second portion has the sequence of SEQ ID NO:8.

23. The fusion protein of claim 17 wherein the second portion has the sequence of SEQ ID NO:13.

24. The fusion protein of claim 17 wherein the first portion has the sequence of SEQ ID NO:3.

25. The fusion protein of claim 17 wherein the first portion has the sequence of SEQ ID NO:6.

* * * * *

```
                        SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
         (A) LENGTH: 40 amino acids
         (B) TYPE: amino acid
         (D) TOPOLOGY: linear (ii) MOLECULE TYPE: peptide (xi) SEQUENCE DESCRIPTION: SEQ ID NO:1:

Ala Ala Val Ala Leu Leu Pro Ala Val Leu Leu Ala Leu Leu Ala Pro
 1               5                  10                  15

Glu Lys Leu Gly Glu Arg Asp Asp Thr Ile Pro Pro Glu Tyr Arg Glu
            20                  25                  30
```

```
Leu Leu Glu Lys Lys Thr Gly Val
         35                  40
```

(2) INFORMATION FOR SEQ ID NO:2:

(i) SEQUENCE CHARACTERISTICS:
        (A) LENGTH: 40 amino acids
        (B) TYPE: amino acid
        (D) TOPOLOGY: linear (ii) MOLECULE TYPE: peptide (xi) SEQUENCE DESCRIPTION: SEQ ID NO:2:

```
Ala Ala Val Ala Leu Leu Pro Ala Val Leu Leu Ala Leu Leu Ala Pro
 1               5                  10                  15

Glu Lys Leu Ala Glu Arg Ala Asp Ala Ala Pro Glu Ala Ala Glu
             20                  25                  30

Leu Leu Glu Lys Lys Thr Gly Val
         35                  40
```

(2) INFORMATION FOR SEQ ID NO:3:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:3:

```
Ala Ala Val Ala Leu Leu Pro Ala Val Leu Leu Ala Leu Leu Ala Pro
 1               5                  10                  15
```

(2) INFORMATION FOR SEQ ID NO:4:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (B) LOCATION: 1...1
        (D) OTHER INFORMATION: where Xaa at position 1 is Glu, Asp, or Lys
        (B) LOCATION: 2...2
        (D) OTHER INFORMATION: where Xaa at position 2 is Lys, Glu, Ala,
            or Asn
        (B) LOCATION: 5...5
        (D) OTHER INFORMATION: where Xaa at position 5 is Glu, Lys, or Ile
        (B) LOCATION: 6...6
        (D) OTHER INFORMATION: where Xaa at position 6 is Arg, Lys, or Asp
        (B) LOCATION: 7...7
        (D) OTHER INFORMATION: where Xaa at position 7 is Asp, or Glu
        (B) LOCATION: 8...8
        (D) OTHER INFORMATION: where Xaa at position 8 is Asp, Val, Ser,
            Gly, or Glu
        (B) LOCATION: 13...13
        (D) OTHER INFORMATION: where Xaa at position 13 is Glu, Lys, or
            Asp
        (B) LOCATION: 15...15
        (D) OTHER INFORMATION: where Xaa at position 15 is Arg, Lys, or
            Gln
        (B) LOCATION: 16...16
        (D) OTHER INFORMATION: where Xaa at position 16 is Glu, His, Lys,
            or Leu
        (B) LOCATION: 19...19
        (D) OTHER INFORMATION: where Xaa at position 19 is Glu, Asp, Asn,
            Ala, or Val
        (B) LOCATION: 20...20
        (D) OTHER INFORMATION: where Xaa at position 20 is Lys, Asp, Gln,
            Asn, Thr, or Met

```
        (B) LOCATION: 21...21
        (D) OTHER INFORMATION: where Xaa at position 21 is Lys, Asp, Glu,
            Gly, or Asn
        (B) LOCATION: 22...22
        (D) OTHER INFORMATION: where Xaa at position 22 is Thr, Glu, Gly,
            or Lys
        (B) LOCATION: 23...23
        (D) OTHER INFORMATION: where Xaa at position 23 is Gly, Ala, Glu,
            Gln, Lys, or Asp
        (B) LOCATION: 24...24
        (D) OTHER INFORMATION: where Xaa at position 24 is Val, Ile, Asp,
            or Gly (xi) SEQUENCE DESCRIPTION: SEQ ID NO:4:

Xaa Xaa Leu Gly Xaa Xaa Xaa Xaa Thr Ile Pro Pro Xaa Tyr Xaa Xaa
 1               5                   10                  15

Leu Leu Xaa Xaa Xaa Xaa Xaa Xaa
            20

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:5:

Ser Phe Leu Leu Arg
 1               5

(2) INFORMATION FOR SEQ ID NO:6:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (xi) SEQUENCE DESCRIPTION: SEQ ID NO:6:

Arg Gln Ile Lys Ile Trp Phe Gln Asn Arg Arg Met Lys Trp Lys Lys
 1               5                   10                  15

(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:7:

Leu Leu Val Tyr
 1

(2) INFORMATION FOR SEQ ID NO:8:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:8:

Glu Glu Leu Gly Lys Arg Glu Val Thr Ile Pro Pro Lys Tyr Arg Glu
 1               5                   10                  15
```

```
Leu Leu Glu Lys Lys Glu Gly Ile
            20

(2) INFORMATION FOR SEQ ID NO:9:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:9:

Glu Glu Leu Gly Lys Arg Glu Ser Thr Pro Pro Lys Tyr Lys Glu
 1               5                  10                  15

Leu Leu Asn Lys Glu Glu Gly Ile
            20

(2) INFORMATION FOR SEQ ID NO:10:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:10:

Glu Glu Leu Gly Lys Arg Glu Val Thr Leu Pro Pro Lys Tyr Arg Glu
 1               5                  10                  15

Leu Leu Asp Lys Lys Glu Gly Ile
            20

(2) INFORMATION FOR SEQ ID NO:11:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:11:

Glu Glu Leu Gly Lys Arg Glu Val Thr Ile Pro Pro Lys Tyr Arg Glu
 1               5                  10                  15

Leu Leu Glu Lys Lys Thr Gly Val
            20

(2) INFORMATION FOR SEQ ID NO:12:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:12:

Glu Ala Leu Gly Ile Lys Glu Gly Thr Ile Pro Pro Glu Tyr Arg Lys
 1               5                  10                  15

Leu Leu Glu Lys Asn Glu Ala Ile
            20

(2) INFORMATION FOR SEQ ID NO:13:

(i) SEQUENCE CHARACTERISTICS:
```

(A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:13:

Asp Lys Leu Gly Glu Arg Asp Asp Thr Ile Pro Pro Glu Tyr Arg His
 1               5                  10                  15

Leu Leu Asp Asp Asn Gly Gln Asp
            20

(2) INFORMATION FOR SEQ ID NO:14:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:14:

Asp Lys Leu Gly Glu Arg Asp Asp Thr Ile Pro Pro Lys Tyr Gln His
 1               5                  10                  15

Leu Leu Asp Asp Asn Lys Glu Gly
            20

(2) INFORMATION FOR SEQ ID NO:15:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:15:

Asp Lys Leu Gly Glu Arg Asp Asp Thr Ile Pro Pro Glu Tyr Arg His
 1               5                  10                  15

Leu Leu Asp Lys Asp Glu Glu Gly
            20

(2) INFORMATION FOR SEQ ID NO:16:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:16:

Asp Lys Leu Gly Glu Arg Asp Asp Thr Ile Pro Pro Glu Tyr Arg His
 1               5                  10                  15

Leu Leu Asp Gln Gly Glu Gln Asp
            20

(2) INFORMATION FOR SEQ ID NO:17:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:17:

```
Glu Lys Leu Gly Glu Arg Asp Asp Thr Ile Pro Pro Glu Tyr Arg His
1               5                   10                  15

Leu Leu Asp Asn Asp Gly Lys Asp
                20
```

(2) INFORMATION FOR SEQ ID NO:18:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (B) LOCATION: 1...1
        (D) OTHER INFORMATION: where Xaa at position 1 is Glu, Asp, or
            Lys
        (B) LOCATION: 2...2
        (D) OTHER INFORMATION: where Xaa at position 2 is Lys, Glu, Ala,
            or Asn
        (B) LOCATION: 5...5
        (D) OTHER INFORMATION: where Xaa at position 5 is Glu, Lys, or
            Ile
        (B) LOCATION: 6...6
        (D) OTHER INFORMATION: where Xaa at position 6 is Arg, Lys, or
            Asp
        (B) LOCATION: 7...7
        (D) OTHER INFORMATION: where Xaa at position 7 is Asp, or Glu
        (B) LOCATION: 8...8
        (D) OTHER INFORMATION: where Xaa at position 8 is Asp, Val, Ser,
            Gly, or Glu
        (B) LOCATION: 13...13
        (D) OTHER INFORMATION: where Xaa at position 13 is Glu, Lys, or
            Asp
        (B) LOCATION: 15...15
        (D) OTHER INFORMATION: where Xaa at position 15 is Arg, Lys, or
            Gln
        (B) LOCATION: 16...16
        (D) OTHER INFORMATION: where Xaa at position 16 is Glu, His, Lys,
            or Leu
        (B) LOCATION: 19...19
        (D) OTHER INFORMATION: where Xaa at position 19 is Glu, Asp, Asn,
            Ala, or Val (xi) SEQUENCE DESCRIPTION: SEQ ID NO:18:

```
Xaa Xaa Leu Gly Xaa Xaa Xaa Xaa Thr Ile Pro Pro Xaa Tyr Xaa Xaa
1               5                   10                  15

Leu Leu Xaa
```